US006776613B2

United States Patent
Orikasa (10) Patent No.: US 6,776,613 B2
(45) Date of Patent: Aug. 17, 2004

(54) ORTHODONTIC BRACKET (75) Inventor: Masaaki Orikasa, Fukushima (JP)

(73) Assignee: Tomy Incorporated, Fukushima (JP)

( * ) Notice: Subject to any disclaimer, the term of this patent is extended or adjusted under 35 U.S.C. 154(b) by 52 days.

(21) Appl. No.: 10/227,415

(22) Filed: Aug. 26, 2002

(65) Prior Publication Data
US 2003/0039938 A1 Feb. 27, 2003

(30) Foreign Application Priority Data
Aug. 24, 2001 (JP) ..................................... P2001-253934

(51) Int. Cl.[7] .................................................. A61C 3/00
(52) U.S. Cl. .......................................... 433/11; 433/13
(58) Field of Search ................................ 433/8, 10, 11, 433/13, 14, 17

(56) References Cited

U.S. PATENT DOCUMENTS

| 5,108,285 A | 4/1992 | Tuneberg |
| 5,224,858 A * | 7/1993 | Hanson ........................ 433/10 |
| 5,288,229 A * | 2/1994 | Huff et al. ..................... 433/17 |
| 5,474,445 A | 12/1995 | Voudouris |
| 5,562,444 A * | 10/1996 | Heiser et al. ................. 433/11 |
| 5,630,716 A | 5/1997 | Hanson |
| 5,913,680 A * | 6/1999 | Voudouris ..................... 433/10 |
| 6,071,119 A | 6/2000 | Christoff et al. |
| 6,257,883 B1 | 7/2001 | Voudouris |

FOREIGN PATENT DOCUMENTS

EP          1 090 604 A2     4/2001

* cited by examiner

Primary Examiner—Todd E. Manahan
(74) Attorney, Agent, or Firm—Sughrue Mion, PLLC

(57) ABSTRACT

An orthodontic bracket has a front side part, a bump portion, an inner side part which are formed on a ceiling face of a guide portion in such a manner that the front side part, the bump portion, the inner side part are formed in order in a guiding direction to which a clip is guided by the guide portion. The orthodontic bracket further has a sliding-rotation supporter provided at the lower end of the clip. When the sliding-rotation supporter slides on the ceiling face and gets over the bump portion from the front side part to reach the inner side part of the ceiling face, the clip can press the archwire down toward the bottom of the archwire slot.

8 Claims, 10 Drawing Sheets

ORTHODONTIC BRACKET

BACKGROUND OF THE INVENTION

1. Field of the Invention

The present invention relates to an orthodontic bracket which, in particular, enables to secure a proper pressing-down force to an archwire supported in an archwire slot for correcting irregular rows of teeth or twisted teeth.

2. Description of the Related Art

U.S. Pat. No. 5,108,285 discloses a self-ligation bracket as an orthodontic bracket. This self-ligation bracket is a PASSIVE TYPE bracket where an opening of an archwire slot is closed with a rotating clip for the archwire not to get out from the archwire slot.

The PASSIVE TYPE bracket is that the clip serves as a cap to form a through-hole of the archwire. In contrast, an ACTIVE TYPE bracket is that the clip bends itself to press down the archwire to a bottom of the slot.

In this PASSIVE TYPE bracket, thickness of the clip is made large to increase rigidity so that the archwire slot is closed with the clip of high rigidity to avoid the archwire from getting out of the slot.

According to this PASSIVE TYPE bracket, when setting a thin and round archwire (0.014 or 0.016 inch diameter) used at an initial stage of the treatment in an archwire slot of 0.018 inch size, even if closing the opening of the archwire slot with the clip, the clip does not come into contact with the thin and round archwire.

Therefore, since the archwire can be slid in the interior of the archwire slot, a friction free condition can be obtained which is required to the thin archwire used at the initial stage of the treatment.

On the other hand, if setting a comparatively thick and square archwire (0.016 inch×0.022 inch or 0.017 inch×0.025 inch) used at the second and final stage of the treatment in the archwire slot of 0.018 inch size, and closing the opening of the archwire slot with the clip, the clip comes into contact with the archwire.

However, since the clip has the high rigidity, the archwire is firmly urged by the clip and is made tight within the slot, so that the archwire cannot be slid in the interior of the archwire slot. Further, the clip of high rigidity cannot be expected to be bent, and for example, even if a tooth is strongly twisted as a rotation control, the clip itself cannot be expected to press down the wire into the slot.

For solving such inconveniences, it may be assumed that the clip is made small in thickness. By making the clip thin, it is possible that flexibility of the clip is increased, and the pressing force of the archwire by the clip is made small although the archwire comes into contact with the clip, so that the archwire is made slid within the slot.

However, if making the clip thin, there is a problem that when adding the strong rotation to the clip from the archwire, the clip opens unexpectedly by pushing-up force.

SUMMARY OF THE INVENTION

The invention has been established in view of the above mentioned problems, and it is an object of the invention to offer such an orthodontic bracket enabling the archwire to slide within the archwire slot even when the clip comes into contact with the archwire, and enabling to cause the clip to bent so as to press down the archwire toward the bottom of the slot even when the strong rotation is added.

For accomplishing the object of the invention, the invention as set forth in a first aspect is an orthodontic bracket comprising:
- a base firmly attachable directly or indirectly to teeth surfaces;
- a bracket main body disposed on one side of the base;
- a groove-shaped archwire slot formed along a mesiodistal direction in the bracket main body, for holding an archwire therein;
- a clip having a substantially belt shape and being curved substantially in a U-shape for covering at least one part of an opposite side to the base in the archwire slot, the clip having a catching end portion provided at an upper part thereof and a sliding-rotation supporter provided at a lower part thereof;
- a cover portion supported by the bracket main body, under which the catching end portion gets into and engages with; and
- a guide portion formed in at least one of the bracket main body and the base and along a tooth axial direction crossing with the archwire slot, for guiding the clip in a guiding direction, the guide portion having a front side part, a bump portion and an inner side part, which are provided in order in the guiding direction, at a ceiling face thereof,
- wherein when the sliding-rotation supporter slides on the ceiling face and gets over the bump portion of the ceiling face from the front side part to reach the inner side part of the ceiling face, the clip enables to press down the archwire toward a bottom of the archwire slot.

Herein, the orthodontic bracket according to the invention includes an embodiment that the bracket main body is secured to the face-shaped base attachable to the teeth surfaces, or an embodiment that the bracket main body is welded, via the base, to a band attached to the teeth surfaces.

In the thus structured orthodontic bracket, when the sliding-rotation supporter of the clip gets over the bump portion of the ceiling face from the front side part to reach the inner side part of the ceiling face, the orthodontic bracket is structured so that the catching end portion of the clip gets into under the cover portion of the bracket.

Therefore, even if the strong rotation is effected to the clip from the archwire, the catching end portion of the clip is prevented from getting out of the cover portion and opening.

In the orthodontic bracket as set forth in a second aspect, according to the orthodontic bracket of the first aspect, it is preferable that the ceiling face inclines so that the inner side part of the ceiling face comes nearer to the base than the front side part of the ceiling face.

The orthodontic bracket is structured so that, by tilting the ceiling face, it is brought nearer to the base toward the inner side part in the guiding direction. Therefore, the more the sliding-rotation supporter of the clip is pressed toward the inner side part in the guiding direction, the more the clip presses down the archwire to the bottom of the archwire slot.

In the orthodontic bracket as set forth in a third aspect, according to the orthodontic bracket of the second aspect, it is preferable that the ceiling face has a stepwise portion. Therefore, when the sliding-rotation supporter pressed toward the inner side part in the guiding direction gets over the stepwise portion, the sliding-rotation supporter has less possibility to return to an initial position, thereby to securely maintain a condition where the archwire is pressed down to the bottom of the archwire slot.

In the orthodontic bracket as set forth in a fourth aspect, according to the orthodontic bracket of the first aspect, it is preferable that when the sliding-rotation supporter is positioned at a front of the bump portion, the clip enables to rotate with respect to the bracket main body.

By arranging the sliding-rotation supporter in the front of the bump portion, the clip can be rotated with respect to the bracket main body. Therefore, the archwire can be easily detachably attached to the archwire slot, and this kind of self-ligation brackets can be reduced in size.

In the orthodontic bracket as set forth in a fifth aspect, according to the orthodontic bracket of the fourth aspect, it is preferable that the clip has a curved portion, and when the clip rotates with respect to the bracket main body, the curved portion comes into contact with an edge of the base and controls a rotation of the clip.

By controlling the rotation of the clip with the edge of the base, the clip does not get out of the bracket main body. Therefore, the archwire can be more easily detachably attached to the archwire slot.

In the orthodontic bracket as set forth in a sixth aspect, according to the orthodontic bracket of the first aspect, it is preferable that the clip has a releasing recess at an upper part thereof.

Herein, as the releasing recess, a concave or a through-hole may be exemplified. Therefore, if an operator hooks it at his fingers, nails or the distal end of the instrument, the catching end portion and the covering portion can be engaged more securely or released more easily, and the clip can be rotated with respect to the bracket main body.

In the orthodontic bracket as set forth in a seventh aspect, according to the orthodontic bracket of the first aspect, it is preferable that the bracket main body has a tube, and the clip is arranged to follow an outer circumference of the tube.

In the orthodontic bracket as set forth in an eighth aspect, according to the orthodontic bracket of the first aspect, it is preferable that the clip has a tab at an upper part thereof and the cover portion has a groove for holding the tab of the clip therein.

In this invention, with respect to the tab held in the groove formed in the cover portion, if the operator hooks the tab at his fingers, nails or the distal end of the instrument to press down the tab, the catching end portion and the covering portion can be engaged more securely or released more easily.

DETAILED DESCRIPTION OF THE INVENTION

Detailed explanation will be made to embodiments of the invention with reference to the attached drawings. In each of the embodiments, members explained in FIG. 1 will be given the same or corresponding numerals for simplifying or omitting the explanation.

Herein, in each of under shown embodiments, as the orthodontic bracket, twin brackets (brackets having the two cover portions) are exemplified, but the invention is also applicable to a single bracket, and is not limited to the twin brackets only.

In addition, in the following embodiments, the orthodontic bracket used to a labial side (a lip side) is shown, but also applicable to a lingual side (a tongue side)

Figure 1:
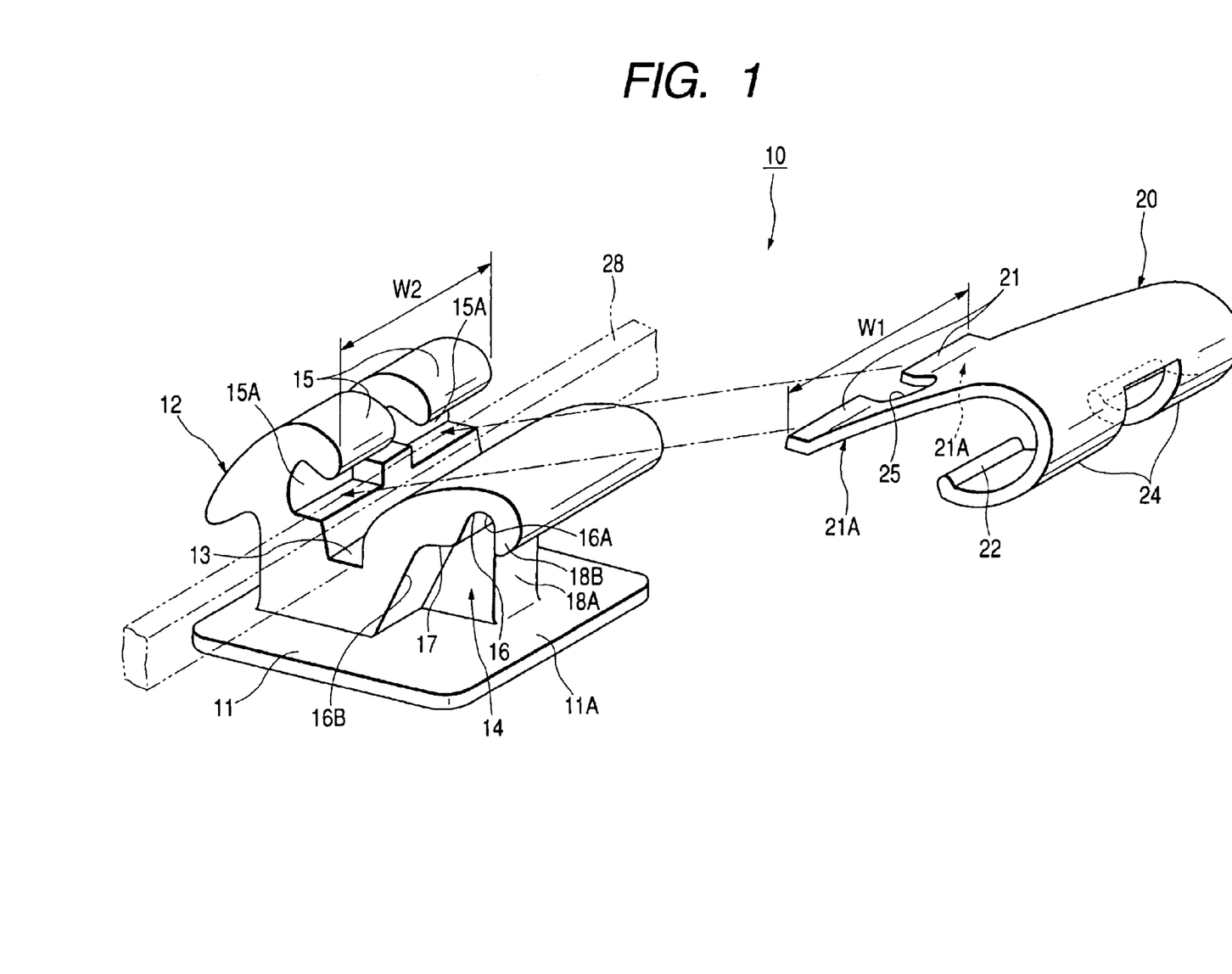
FIG. 1 is a perspective view showing an orthodontic bracket (the first embodiment) according to the invention.

As shown in FIG. 1, an orthodontic bracket 10 as a first embodiment according to the invention has a face-shaped base 11 firmly attachable to teeth surfaces, a bracket main body 12 disposed on one side of the base 11, a groove-shaped archwire slot 13 formed in the bracket main body 12, a guide portion 14 formed in at least either of the bracket main body 12 and the base 11 and along a tooth axial direction crossing with the archwire slot 13, and a substantially belt-shaped clip 20 guided by the guide portion 14 in a guiding direction.

The archwire slot 13 is formed along the mesiodistal direction in the bracket main body 12.

In the orthodontic bracket 10, the clip 20 is curved substantially in U-shape as covering at least one part of an opposite side to the base in the archwire slot 13. A catching end portion 21 is provided at an upper part along the length direction of the clip 20 and gets into a catching groove 15A under a cover portion 15 supported by the bracket main body 12.

Herein, the opposite side to the base is generally designated as the labial side (the lip side), but in a case of the lingual bracket, it is designated as the lingual side (the tongue side).

Further, the orthodontic bracket 10 has a front side part 16A, a bump portion 17 and an inner side part 16B which are formed on a ceiling face 16 in the guide portion 14 in such manner that the front side part 16A, the bump portion 17 and the inner side part 16B are provided in order in the guiding direction, and a sliding-rotation supporter 22 provided at the lower end part along the length direction of the clip 20. When the sliding-rotation supporter 22 slides on the ceiling face 16 and gets over the bump portion 17 from the front side part 16A to reach the inner side part 16B, a pressing part 21A of the clip 20 enables to press down the archwire 28 toward the bottom of the archwire slot 13. By bending downward the pressing part 21A, an archwire 28 can be efficiently pressed down.

In addition, the orthodontic bracket 10 has an occlusal tie wing 18 (See FIG. 2) which is supported at its center by one piece of a central foot 18A.

The ceiling face 16 inclines so that the inner side part 16B comes nearer to the base 11 than the front side part 16A.

Therefore, the more the sliding-rotation supporter 22 of the clip 20 is pressed toward the inner side part 16B in the guiding direction, the more the clip 20 presses down the archwire 28 to the bottom of the archwire slot 13.

The clip 20 is formed to be almost U-shape with, e.g., a spring thin steel of high corrosion resistance of 0.1 to 0.2 mm thickness. When the sliding-rotation supporter 22 is positioned in front of the bump portion 17, the clip 20 rotates around the occlusal tie wing 18, so that it opens the archwire slot 13 and makes the archwire 28 (see FIG. 4) easy to attach and detach.

When the clip 20 rotates with respect to the bracket main body 12 and enters a slot-opened condition, a curved portion 24 of the clip 20 comes into contact with an edge 11A of the base 11, and controls the rotation of the clip 20, thereby enabling to avoid the clip 20 from getting out of the bracket main body 12.

The clip 20 is provided with a releasing recess 25 (FIG. 9) for catching a desired instrument (not shown). Therefore, if an operator hooks it at his fingers, nails or the distal end of the instrument, the catching end portion 21 of the clip 20 and the catching groove 15A of the covering portion 15 can be mutually engaged more securely or released more easily.

In addition, the width W1 of the clip 20 may be the same as or projected than the width W2 of the bracket main body 12.

Actuation of the working of the orthodontic bracket 10 will be explained with reference to FIGS. 2 to 4 of the attached drawings.

Figure 2:
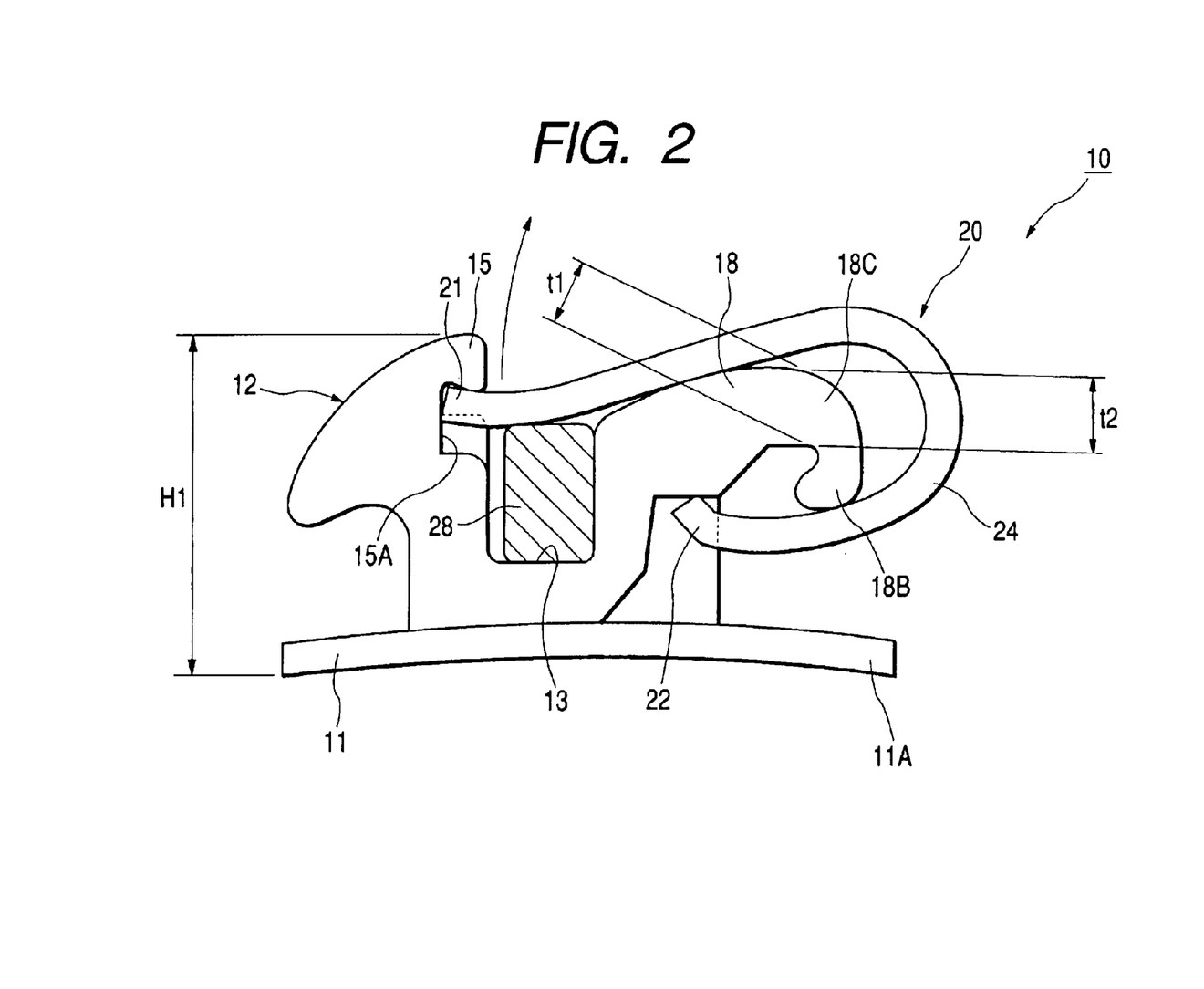
FIG. 2 is a view explaining the work of the first embodiment according to the invention.

FIG. 2 shown a state where the clip 20 is closed, that is, the catching end portion 21 of the clip 20 gets into and engages with the catching groove 15A under the cover portion 15, and a nail-shaped sliding-rotation supporter 22 of the clip 20 gets over the bump portion 17 from the front side part 16A to reach the inner side part 16B.

Under this state, when the sliding-rotation supporter 22 of the clip 20 strongly comes into contact with the ceiling face 16, the sliding-rotation supporter 22 receives a force pressing the sliding-rotation supporter 22 down. This force is transmitted to the catching end portion 21 via the curved portion 24, and can press down the archwire 28 toward the bottom of the archwire slot 13 by means of a portion near the catching end portion 21.

Herein, if the catching end portion 21 is formed with the pressing portion 21A (a bent part of facing downward), the archwire 28 can be pressed down more efficiently toward the bottom of the archwire slot 13.

Further, even if a rotation force works on the clip 20 from the archwire 28 to tilt up the clip 20 as an arrow, it is possible to keep a condition where the catching end portion 21 of the clip 20 engages with the catching groove 15A, so that the clip 20 never gets out from the bracket main body 12.

Since the clip 20 never gets out from the bracket main body 12, the clip 20 can be made thin, so that the flexibility of the clip 20 (that is, the pressing force of the clip 20 can be weakened) can be increased. If the archwire 28 is pressed down to the bottom of the archwire slot 13 by the elasticity of the clip 20, the correcting force for the teeth can also use the elasticity of the clip 20 other than the archwire 28, and the archwire 28 can be slid as needed.

Thereby, it is possible to provide the ACTIVE TYPE bracket enabling to shorten a treatment period and improve a treatment precision.

In addition, the sliding-rotation supporter 22 of the clip 20 gets over the bump portion 17 from the front side part 16A to reach the inner side part 16B under the occlusal tie wing 18, so that the clip 20 can close the archwire slot 13. Therefore, it is no longer necessary guide one end of the clip through under the archwire slot as this kind of conventional self-ligation brackets. Therefore, a height H1 of the orthodontic bracket 10 can be restrained to be lower.

Figure 3:
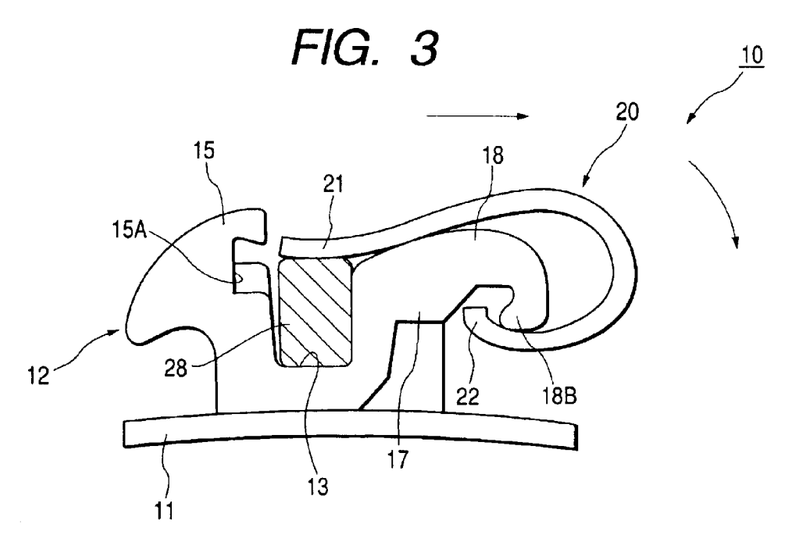
FIG. 3 is a view explaining the work of the first embodiment according to the invention.

In FIG. 3, the clip 20 is slid in an arrow direction (the occlusal direction) until a position, where the front end 21 (the catching end portion) of the clip 20 gets out from the catching groove 15A, and at the same time the sliding-rotation supporter 22 of the clip 20 gets out from the bump portion 17. Under this condition where the sliding-rotation supporter 22 of the clip 20 is engaged with a projection 18B of the occlusal tie wing 18, the clip 20 is rotated in the arrow direction (in the drawing, a clockwise direction).

Figure 4:
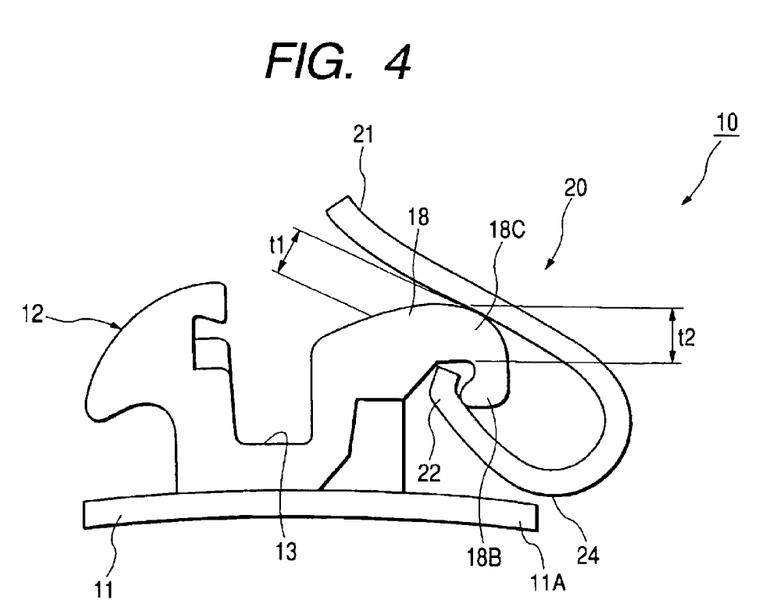
FIG. 4 is a view explaining the work of the first embodiment according to the invention.

In FIG. 4, the clip 20 rotates until an open state to make the archwire slot 13 opened. At this time, the curved portion 24 of the clip 20 comes into contact with the edge 11A of the base 11 for controlling the rotation of the clip 20.

In addition, the relation between the thickness t1 and t2 of the bracket main body 12 satisfies t1>t2. This relation prevents the clip 20 to rotate in a counterclockwise direction (that is, in the closed direction) by means of a projection 18C of the occlusal tie wing 18.

Thus, the clip 20 can be kept opened, and the archwire 28 can be easily detachably attached to the archwire slot 13.

According to the orthodontic bracket 10 according to the first embodiment as explained above, it is possible to provide the friction free condition required to the thin archwire at the initial stage of the treatment, and to securely maintain the pressing-down of the archwire positively for the comparatively thick archwire used to the treatment at the second and final stage of the treatment.

In addition, the orthodontic bracket can be slid as needed to the comparatively thick archwire.

Next, explanation will be made to a second embodiment of the orthodontic bracket, referring to FIGS. 5 to 8 of the attached drawings, and to a modified example of the second embodiment, referring to FIG. 9 thereof.

Figure 5:
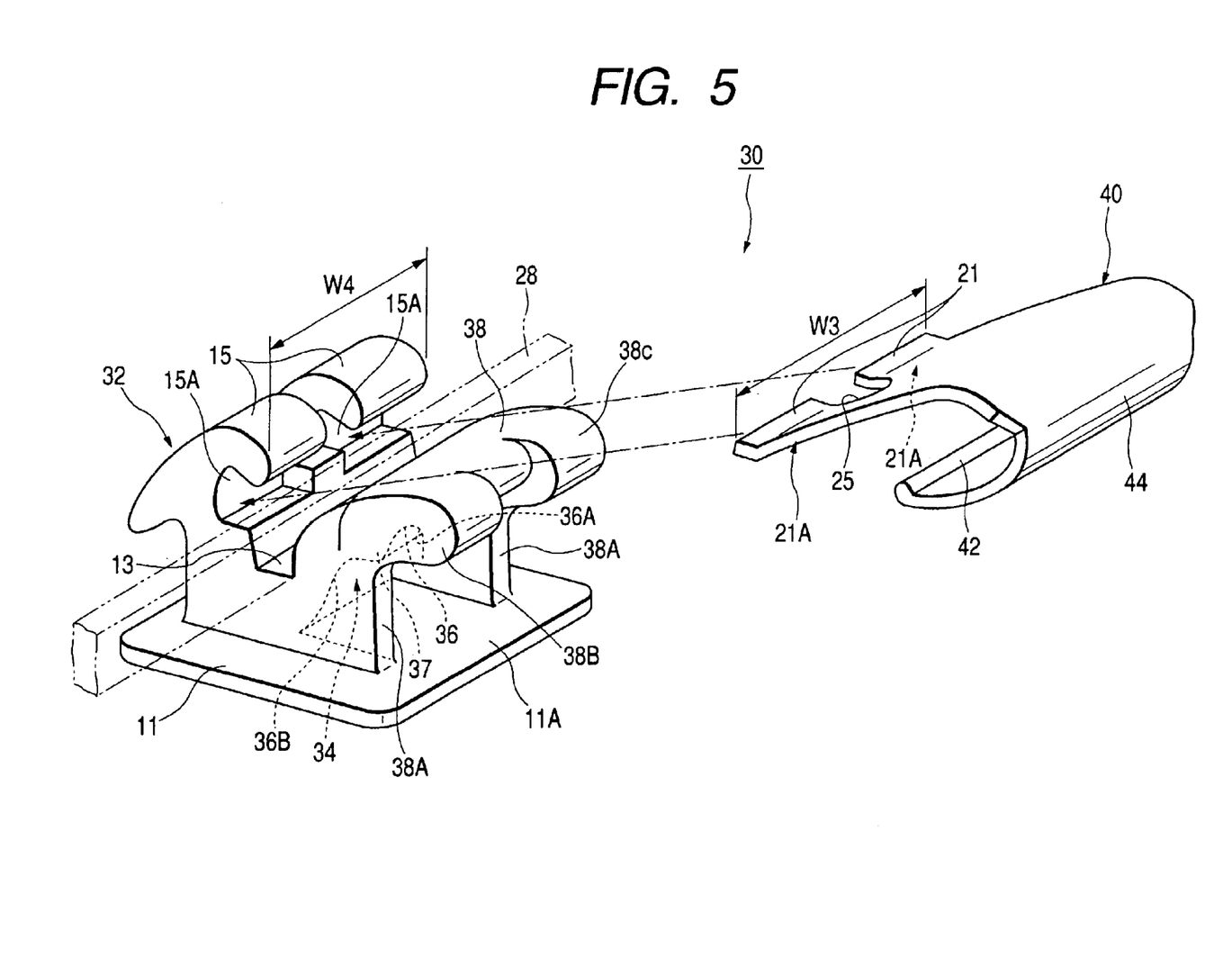
FIG. 5 is a perspective view showing an orthodontic bracket (the second embodiment) according to the invention.

As shown in FIG. 5, an orthodontic bracket 30 as the second embodiment according to the invention has the face-shaped base 11 firmly attachable to teeth surfaces, a bracket main body 32 disposed on one side of the base 11, the groove-shaped archwire slot 13 formed in the bracket main body 32, a guide portion 34 formed in at least either of the bracket main body 32 and the base 11 and along the tooth axial direction crossing with the archwire slot 13, and a substantially belt-shaped clip 40 guided by the guide portion 34 in a guiding direction. The archwire slot 13 is formed along the mesiodistal direction in the bracket main body 32.

In the orthodontic bracket 30, the clip 40 is curved substantially in U-shape as covering at least one part of an opposite side to the base in the archwire slot 13. The catching end portion 21 is provided at an upper part along the length direction of the clip 40 and gets into and engaged with the catching groove 15A under the cover portion 15 supported by the bracket main body 32.

Herein, the opposite side to the base is generally designated as the labial side (the lip side), but in a case of the lingual bracket, it is designated as the lingual side (the tongue side).

Further, the orthodontic bracket 30 has a front side part 36A, a bump portion 37 and an inner side part 36B which are formed on a ceiling face 36 in the guide portion 34 in such a manner that the front side part 36A, the bump portion 37 and the inner side part 36B are provided in order in the guiding direction and a sliding-rotation supporter 42 provided at the lower end part along the length direction of the clip 40. When the sliding-rotation supporter 42 slides on the ceiling face 36 and gets over the bump portion 37 from the front side part 36A to reach the inner side part 36B, the pressing part 21A of the clip 40 enables to press down the archwire 28 toward the bottom of the archwire slot 13.

The orthodontic bracket 30 according to the second embodiment is different from the first embodiment in that the occlusal tie wing 38 is a twin bracket, and the clip 40 enters between foot portions 38A and a pair of tie wings composing the twin bracket, and other structures are the same as those of the first embodiment.

The ceiling face 36 inclines or has a stepwise portion, so that the inner side part 36B in the guiding direction comes nearer to the base 11 than the front side part 36A in the guiding direction.

Therefore, the more the sliding-rotation supporter 42 of the clip 40 is pressed toward the inner side part 36B in the guiding direction, the more the clip 40 presses down the archwire 28 (see FIG. 6) to the bottom of the archwire slot 13.

The clip 40 is formed to be almost U-shape with, e.g., a spring thin steel of high corrosion resistance of 0.1 to 0.2 mm thickness. When the sliding-rotation supporter 42 is positioned in front of the bump portion 37, the clip 40 rotates around the occlusal tie wing 38, so that it opens the archwire slot 13 and makes the archwire 28 (see FIG. 6) easy to attach and detach.

When the clip 40 rotates with respect to the bracket main body 32, and the archwire slot 13 enters an opened condition, the curved portion 44 of the clip 40 comes into contact with the edge 11A of the base 11, and controls the rotation of the clip 40, thereby enabling to detachably attaching the archwire 28 to the archwire slot 13 more easily.

The clip 40 is provided with the releasing recess 25 for catching a desired instrument (not shown). Therefore, if an operator hooks it at his fingers, nails or the distal end of the instrument, the catching end portion 21 of the clip 40 and the catching groove 15A of the covering portion 15 can be mutually engaged more securely or released more easily.

In addition, the width W3 of the clip 40 may be the same as or projected than the width W4 of the bracket main body 12.

Actuation of the working of the orthodontic bracket 30 will be explained with reference to FIGS. 6 to 8 of the attached drawings.

Figure 6:
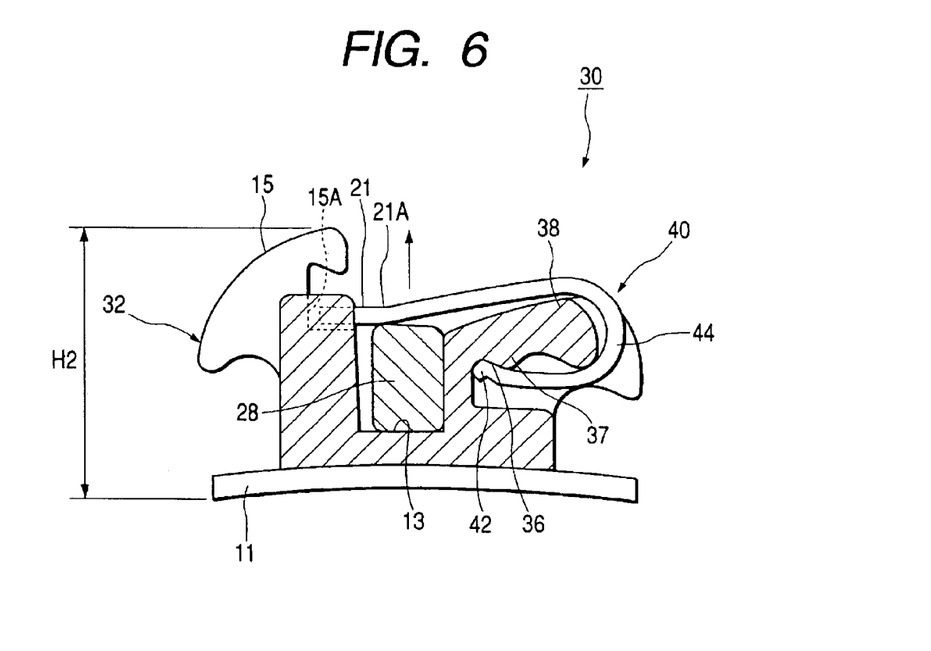
FIG. 6 is a view explaining the work of the second embodiment according to the invention.

FIG. 6 shown a state where the clip 40 is closed, that is, the catching end portion 21 of the clip 40 gets into and engages with the catching groove 15A of the cover portion 15, and the sliding-rotation supporter 42 of the clip 40 gets over the bump portion 37 from the front side part 36A to reach the inner side part 36B.

Under this state, when the sliding-rotation supporter 42 of the clip 40 comes into contact with the ceiling face 36, it receives a force pressing down the sliding-rotation supporter 42. This force is transmitted to the catching end portion 21 via the curved portion 44, and can press down the archwire 28 toward the bottom of the archwire slot 13 by means of the pressing portion 21A of the catching end portion 21.

Herein, if the catching end portion 21 is formed with the pressing portion 21A (a bent part of facing downward), the archwire 28 can be pressed down more efficiently toward the bottom of the archwire slot 13.

Further, even if the rotation force works on the clip 40 from the archwire 28 to tilt up the clip 40 as an arrow, a condition may be kept that the catching end portion 21 of the clip 40 engages with the catching groove 15A, so that the clip 40 never gets out from the bracket main body 32.

Since the clip 40 never gets out from the bracket main body 32, the clip 40 can be made thin, so that the flexibility of the clip 40 (that is, the pressing force of the clip 40 can be weakened) can be increased, and so even if the archwire 28 is pressed down to the bottom of the archwire slot 13 by the elasticity of the clip 40, the archwire 28 can be slid as needed.

In addition, the sliding-rotation supporter 42 of the clip 40 gets over the bump portion 37 from the front side part 36A to reach the inner side part 36B of the ceiling face 36, so that the clip 40 can close the archwire slot 13. Therefore, it is no longer necessary guide one end of the clip through under the archwire slot as this kind of conventional self-ligation brackets. Therefore, the height H2 of the orthodontic bracket 30 can be restrained to be lower.

Figure 7:
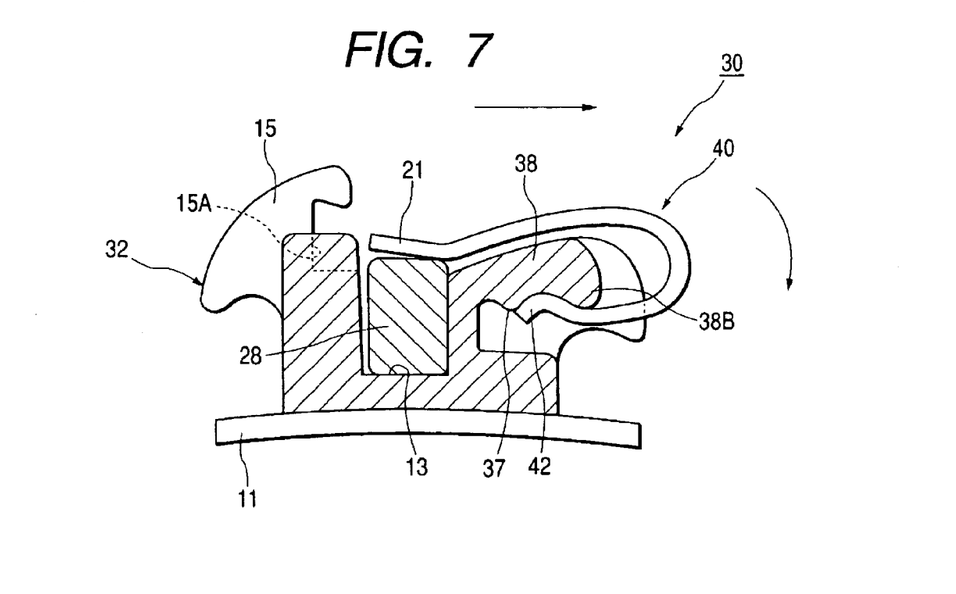
FIG. 7 is a view explaining the work of the second embodiment according to the invention.

In FIG. 7, the clip 40 is slid in an arrow direction (the occlusal direction) until a position where the front end 21 (the catching end portion) of the clip 40 gets out from the catching groove 15A. Under this condition where the sliding-rotation supporter 42 of the clip 40 is engaged with a projection 38B of the occlusal tie wing 38, the clip 40 is rotated in the arrow direction (in the drawing, a clockwise direction).

Figure 8:
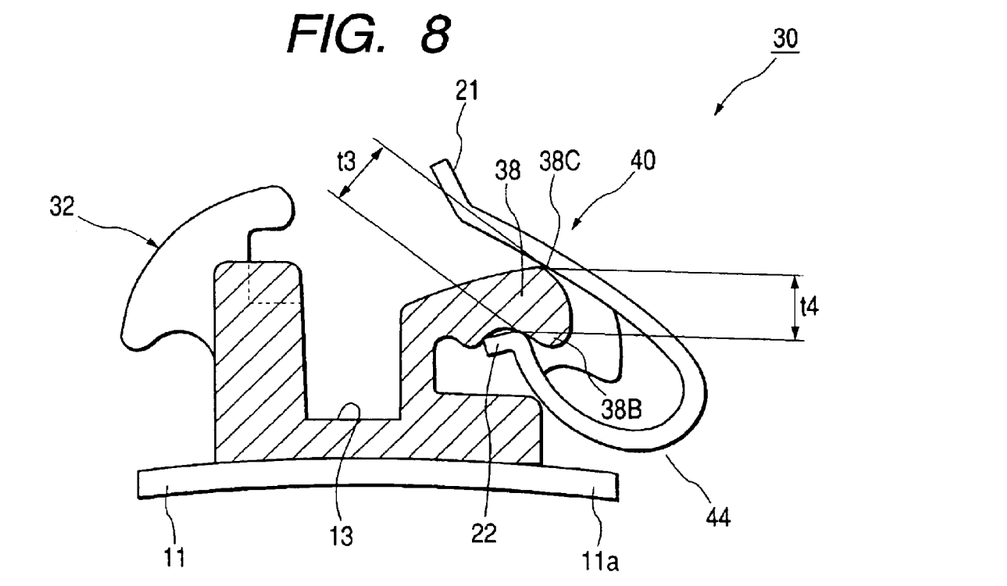
FIG. 8 is a view explaining the work of the second embodiment according to the invention.

In FIG. 8, the clip 40 rotates to bring the archwire slot 13 to the opened condition. At this time, the curved portion 44 of the clip 40 comes into contact with the edge 11A of the base 11 for controlling the rotation of the clip 40.

In addition, the relation between the thickness t3 and t4 of the bracket main body 12 satisfies t3>t4. This relation prevents the clip 20 to rotate in a counterclockwise direction (that is, in the closed direction) by means of a projection 38C of the occlusal tie wing 38.

Thus, the clip 40 can be kept opened, and the archwire 28 can be easily detachably attached to the archwire slot 13.

According to the orthodontic bracket 30 according to the second embodiment as explained above, it is possible to provide the friction free condition required to the thin archwire at the initial stage of the treatment, and to securely maintain the pressing-down of the archwire positively for the comparatively thick archwire used to the treatment at the second and final stage of the treatment.

In addition, the orthodontic bracket can be slid as needed to the comparatively thick archwire.

Figure 9:
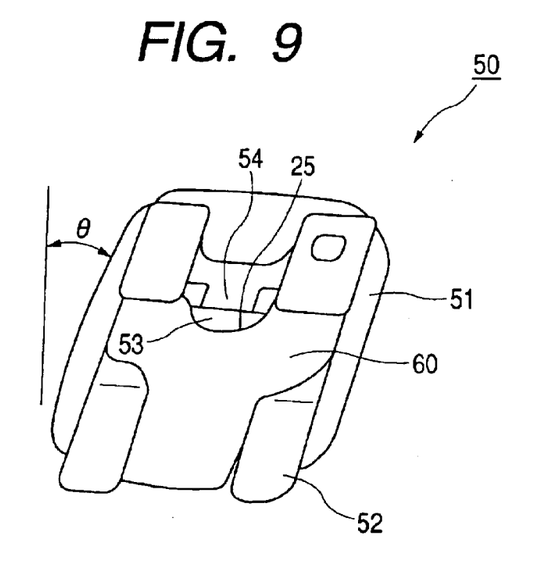
FIG. 9 is a front view showing a modified example of the orthodontic bracket (the second embodiment) according to the invention.

As shown in FIG. 9, a modified example of the second embodiment according to the invention is an orthodontic bracket 50 with angulation where the orthodontic bracket of the second embodiment is inclined at 0°, and other structures are the same as those of the orthodontic bracket 30.

In this orthodontic bracket 50, a base 51, a bracket main body 52 and a clip 60 are inclined at 0° respectively.

In addition, the orthodontic bracket 50 is provided with a slot blocker 54 for the archwire slot 53 of the bracket main body 52, whereby a thin archwire is prevented from getting out of the archwire slot 53 and getting into the catching groove 15A (see FIG. 5).

Herein, it is also possible adopt, as a modified example of the first embodiment, the orthodontic bracket with angulation where the orthodontic bracket 10 of the first embodiment is inclined at 0°.

Incidentally, in each of the above mentioned embodiments, the explanation was made to the examples where the clips 20, 40 were at the occlusal sides, and the catching groove 15A which engages with the front ends of the clips 20, 40 were at the gingival sides, but it is also available that the clips 20, 40 are at the gingival sides, and the catching groove 15A which engages with the front ends of the clips 20, 40 is at the occlusal sides.

In each of the above mentioned embodiments, the explanation was made to the examples where the material of the clips 20, 40 was the spring thin sheet of high corrosion resistance, but specifically, it is also available that the clips 20, 40 are made of a spring stainless steel, Co—Cr alloy, Ni group alloy, β Ti alloy, Ni/Ti super elastic alloy, elastic resin, or rubber plate.

Further, the invention is not limited to the above-mentioned examples, and appropriate modifications or improvements are possible.

For example, in each of the above-mentioned embodiments, the brackets for anterior or bicuspid teeth were exemplified as the orthodontic bracket, but the invention is applicable to a molar bracket shown in FIGS. 10A to 14.

Figure 10A:
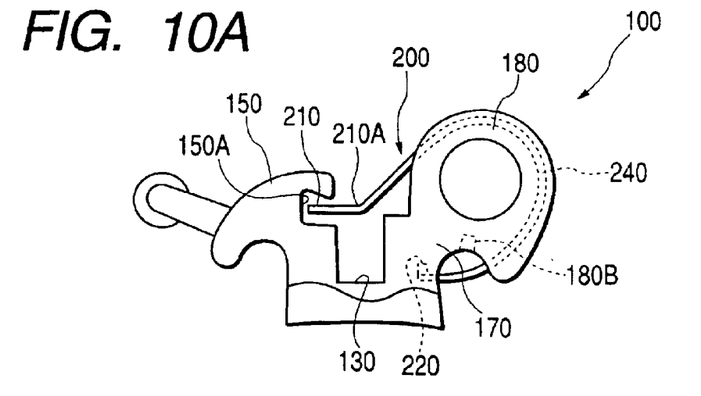
FIGS. 10A–10C are views showing a modified example of the orthodontic bracket according to the invention.
Figure 10B:
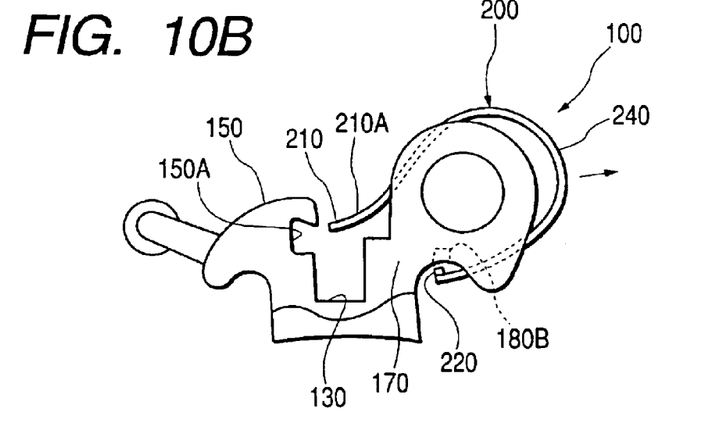
Figure 10C:
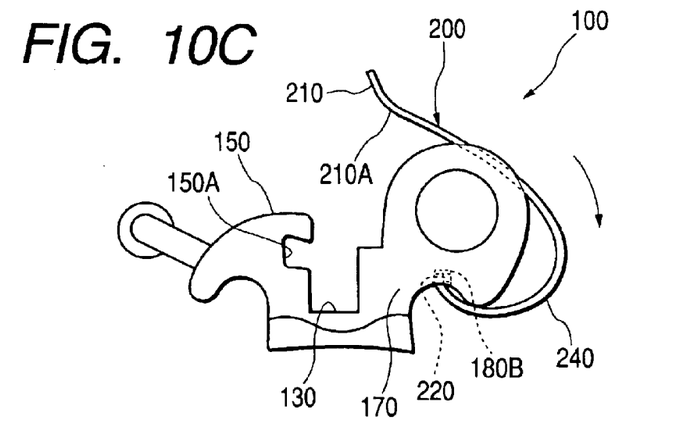

That is, an orthodontic bracket 100 shown in FIGS. 10A–10C is a bracket for molar. FIG. 10A shows a closed state of a clip 200, that is, a catching end portion 210 of the clip 200 gets into and engages with a catching groove 150A under a cover portion 150, and a nail-shaped sliding-rotation supporter 220 formed in the clip 200 gets over the bump portion 170 from a front side part to reach an inner side part of a ceiling face.

In FIG. 10B, the clip 200 is slid in an arrow direction (the occlusal direction) until a position, where the front end 210 (the catching end portion) of the clip 200 gets out from the catching groove 150A, and at the same time the sliding-rotation supporter 220 of the clip 220 gets out from the bump portion 170. Under this condition where the sliding-rotation supporter 220 of the clip 200 is engaged with a catching recess 180B of a round tube 180, the clip 20 is rotated in the arrow direction (in the drawing, a clockwise direction) (see FIG. 10C).

Thereby, the clip 200 rotates till an opened state to make the archwire slot 130 opened. The round tube 180 is inserted with a face bow or a distal of a lip bumper in response to treatment purposes. The clip 200 slidably rotates on the outer circumference of the round tube 180.

Figure 11:
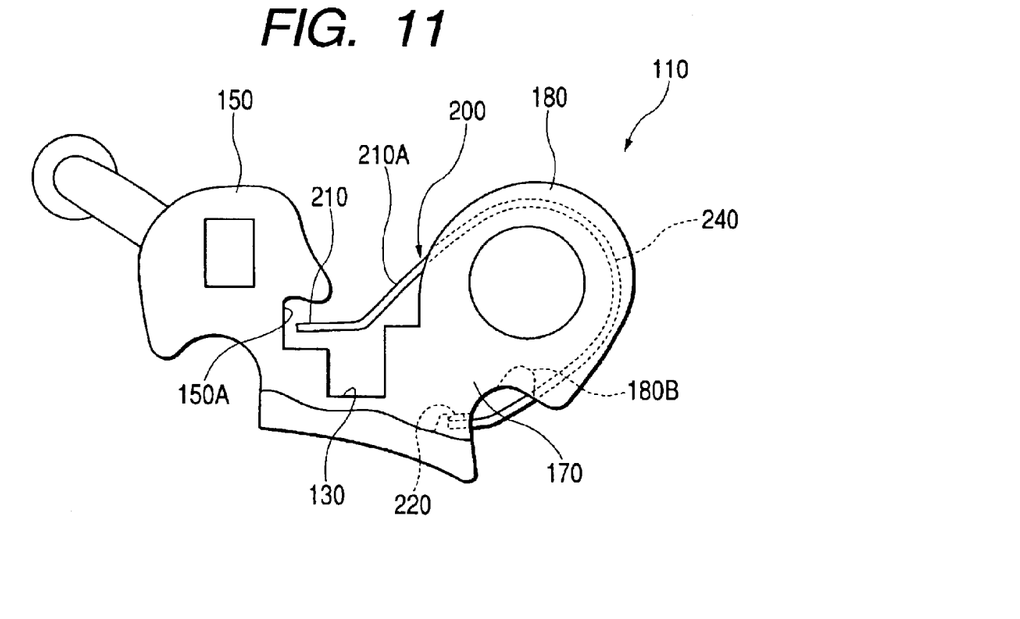
FIG. 11 is a view showing a modified example of the orthodontic bracket according to the invention.

An orthodontic bracket 110 shown in FIG. 11 is an upper first molar triple bracket, and a basic structure is the same as that of the orthodontic bracket 100.

Figure 12:
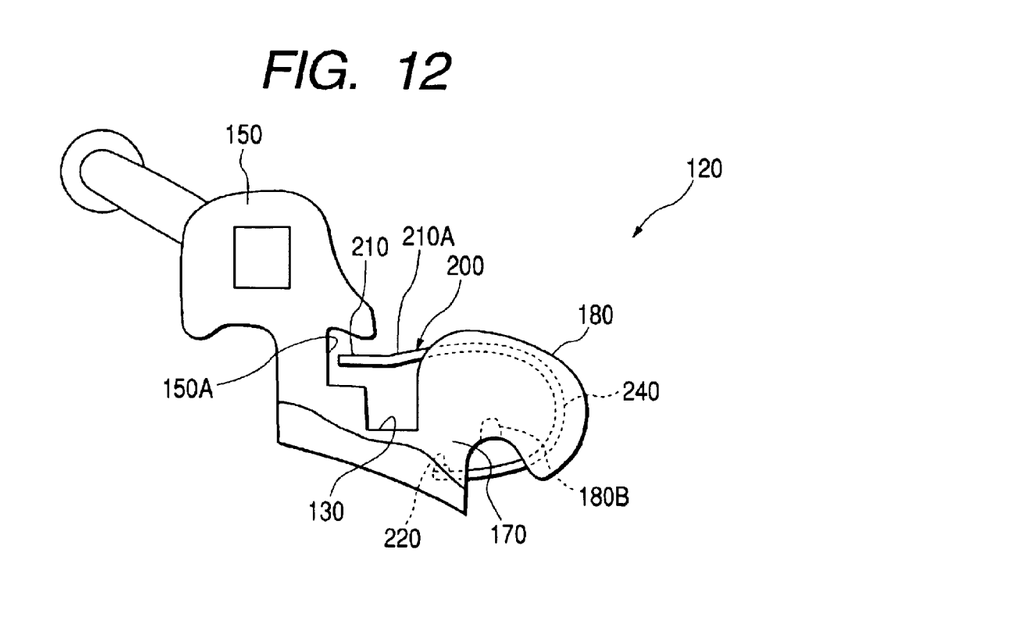
FIG. 12 is a view showing a modified example of the orthodontic bracket according to the invention.

Further, an orthodontic bracket 120 shown in FIG. 12 is a lower twin bracket, and a basic structure is the same as that of the orthodontic bracket 100.

Square tubes of a cover portion 150 shown in FIGS. 11 and 12 are auxiliary tubes used when attaching an auxiliary wire, and in the drawing, those are at the gingival side and may be provided at the occlusal side. In this case, the clip 200 slidably rotates on the outer circumference of the square tube.

Figure 13:
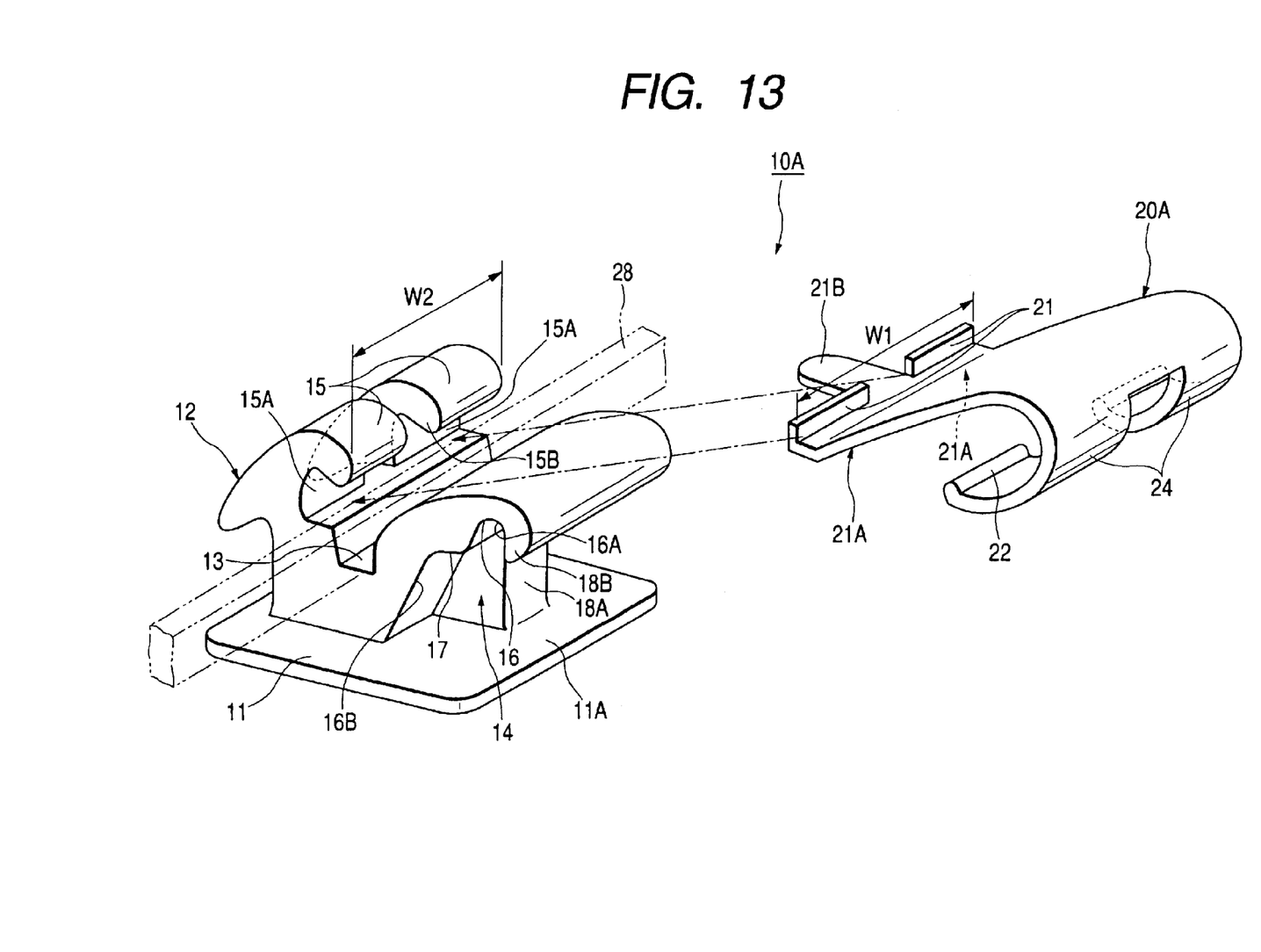
FIG. 13 is a view showing a modified example of the orthodontic bracket according to the invention.
Figure 14:
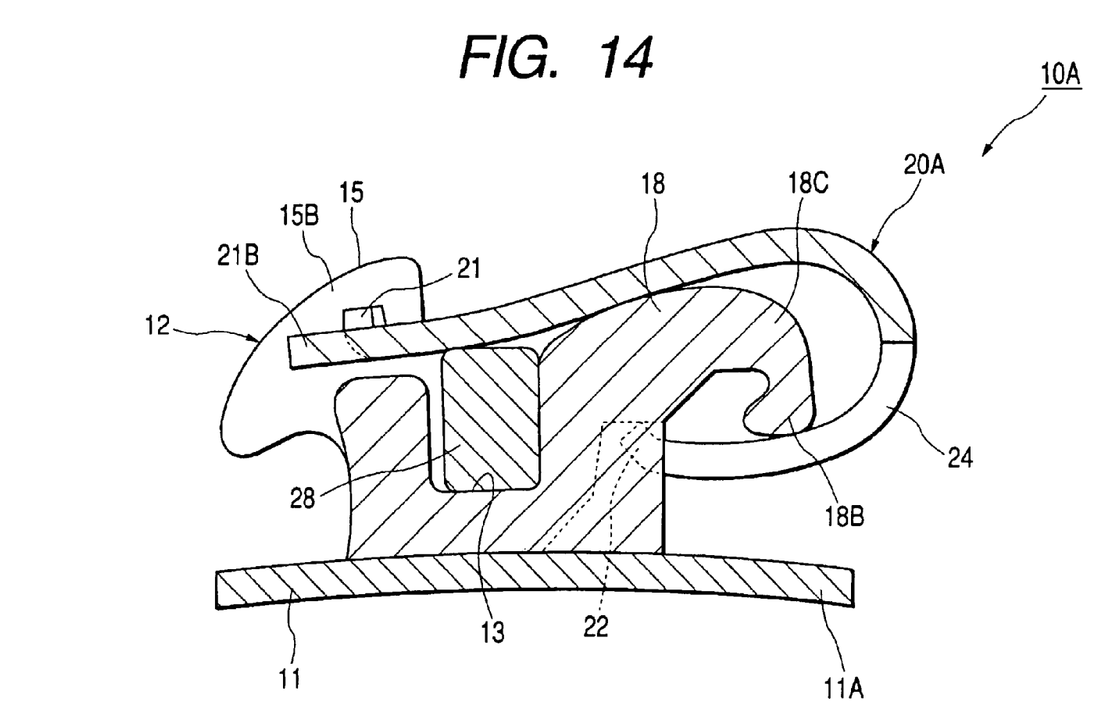
FIG. 14 is a view showing a modified example of the orthodontic bracket according to the invention.

A basic structure of an orthodontic bracket 10A shown in FIGS. 13 and 14 is the same as that of the first embodiment, and is different in that a groove 15B is formed between a pair of cover portions 15, 15, and a tab 21B is provided at an upper end of a clip 20A.

As to this orthodontic bracket 10A, when the catching end portion 21 of the clip 20A is engaged in mesh with the catching groove 15A under the cover portion 15 supported by the bracket main body 12, the tab 21B is held in the groove 15B.

Therefore, according to the orthodontic bracket 10A, if the operator hooks the tab 21B in the groove 15B at his fingers, nails or the distal end of the instrument to press down the tab 21B, the catching end portion 21 and the covering portion 15 can be engaged more securely or released more easily.

In others, as far as materials, shapes, dimensions, figures, numbers, disposing positions, or thickness sizes of the bracket main body or the clip exemplified in each of the above mentioned embodiments may accomplish the invention, they are arbitrary and not limited.

As mentioned above, according to the invention as set forth in the first aspect, when the sliding-rotation supporter of the clip gets over the bump portion of the ceiling face from the front side part to reach the inner side part of the ceiling face, the catching end portion of the clip is engaged with the bracket main body, and at the same time the archwire is pressed down by the clip toward the bottom of the archwire slot.

Since the catching end portion of the clip can be firmly engaged with the bracket main body, even if the strong rotation is effected to the clip from the archwire, it is possible to prevent the catching end portion of the clip from getting out of the bracket main body and opening the clip.

Accordingly, it is possible to reduce the clip thickness for providing flexibility, to press down the archwire toward the bottom of the archwire slot owing to the elasticity of the clip, and to cause the archwire sliding in heavy weight if necessary.

Thereby, since the archwire itself and the elasticity of the clip work synergistically, in comparison with the PASSIVE TYPE bracket which merely closes the archwire slot as conventionally, the treatment period can be shortened and the treatment effect of higher precision is brought about.

According to the invention as set forth in the second aspect, the orthodontic bracket is structured so that, by tilting the ceiling face, it is brought nearer to the base, that is, it is separated further from the archwire slot, toward the inner side part in the guiding direction. Therefore, the more the sliding-rotation supporter of the clip is pressed toward the inner side part in the guiding direction, the more the clip presses down the archwire to the bottom of the archwire slot.

According to the invention as set forth in the third aspect, as the ceiling face has the stepwise portion, when the sliding-rotation supporter is pressed toward the inner side part in the guiding direction and gets over the stepwise portion, the sliding-rotation supporter has less possibility to return to an initial position, thereby to securely maintain a condition where the archwire is pressed down to the bottom of the archwire slot.

According to the invention as set forth in the fourth aspect, by arranging the sliding-rotation supporter in front of the bump portion, the clip can be rotated with respect to the bracket main body. Therefore, the archwire can be easily detachably attached to the archwire slot.

According to the invention as set forth in the fifth aspect, by controlling the rotation of the clip with the edge of the base, the clip does not get out of the bracket main body. Therefore, the archwire can be more easily detachably attached to the archwire slot.

According to the invention as set forth in the sixth aspect, by providing the releasing recess for catching a desired instrument in the clip, if the operator hooks the releasing recess at his fingers, nails or the distal end of the instrument, the catching end portion and the covering portion can be engaged more securely or released more easily.

According to the invention as set forth in the seventh aspect, the clip may be disposed to follow on the outer circumference of the tube.

According to the invention as set forth in the eighth aspect, the clip has a tab at an upper part thereof, and the tab is held in a groove formed in the cover portion, and if the operator hooks the tab at his fingers, nails or the distal end of the instrument to press down the tab, the catching end portion and the covering portion can be engaged more securely or released more easily.

What is claimed is:

1. An orthodontic bracket comprising:
   a base firmly attachable directly or indirectly to teeth surfaces;
   a bracket main body disposed on one side of the base;
   an archwire slot formed along a mesiodistal direction in the bracket main body, for holding an archwire therein;
   a clip being curved substantially in a U-shape for covering at least one part of an opposite side to the base in the archwire slot, the clip having a catching end portion provided at an upper part thereof and a sliding-rotation supporter provided at a lower part thereof;
   a cover portion supported by the bracket main body, under which the catching end portion gets into and engages with; and
   a guide portion formed in at least one of the bracket main body and the base and along a tooth axial direction crossing with the archwire slot, for guiding the clip in a guiding direction, the guide portion having a front side part, a bump portion and an inner side part, which are provided in order in the guiding direction, at a ceiling face thereof,
   wherein when the sliding-rotation supporter slides on the ceiling face and gets over the bump portion of the ceiling face from the front side part in the guiding direction to reach the inner side part of the ceiling face, the clip enables to press down the archwire toward a bottom of the archwire slot.

2. The orthodontic bracket as set forth in claim 1, wherein the ceiling face inclines so that the inner side part comes nearer to the base than the front side part of the ceiling face.

3. The orthodontic bracket as set forth in claim 2, wherein the ceiling face has an inclined portion.

4. The orthodontic bracket as set forth in claim 1, wherein, when the sliding-rotation supporter is positioned at a front side of the bump portion, the clip enables to rotate with respect to the bracket main body.

5. The orthodontic bracket as set forth in claim 4, wherein the clip has a curved portion, and when the clip rotates with respect to the bracket main body, the curved portion comes into contact with an edge of the base and controls a rotation of the clip.

6. The orthodontic bracket as set forth in claim 1, wherein the clip has a releasing recess at an upper part thereof.

7. The orthodontic bracket as set forth in claim 1, wherein the bracket main body has a tube, and the clip is arranged to follow an outer circumference of the tube.

8. The orthodontic bracket as set forth in claim 1, wherein the clip has a tab at an upper part thereof and the cover portion has a groove for holding the tab of the clip therein.

* * * * *